(12) United States Patent
Meiksin (10) Patent No.: US 9,784,718 B2
(45) Date of Patent: Oct. 10, 2017

(54) METHOD AND APPARATUS FOR DETECTION OF STRUCTURAL FAILURE

(71) Applicant: Alertek, LLC, Pittsburgh, PA (US)

(72) Inventor: Zvi H Meiksin, Pittsburgh, PA (US)

(73) Assignee: Alertek, LLC, Pittsburgh, PA (US)

(*) Notice: Subject to any disclaimer, the term of this patent is extended or adjusted under 35 U.S.C. 154(b) by 437 days.

(21) Appl. No.: 14/275,061

(22) Filed: May 12, 2014

(65) Prior Publication Data

US 2014/0320298 A1 Oct. 30, 2014

Related U.S. Application Data (63) Continuation-in-part of application No. 12/151,077, filed on May 3, 2008, now Pat. No. 8,723,673.

(Continued)

(51) Int. Cl.
*G01N 29/14* (2006.01)
*F16B 31/02* (2006.01)
(Continued)

(52) U.S. Cl.
CPC .............. *G01N 29/14* (2013.01); *F16B 31/02* (2013.01); *G01H 1/00* (2013.01); *G01L 1/255* (2013.01);
(Continued)

(58) Field of Classification Search
CPC ........... F16B 31/02; G01H 1/00; G01L 1/255; G01M 5/0041; G01M 5/0066; G01N 2291/105; G01N 29/14; G08B 21/02
See application file for complete search history.

(56) References Cited

U.S. PATENT DOCUMENTS 3,774,443 A 11/1973 Green
4,149,446 A 4/1979 Spengler
(Continued)

FOREIGN PATENT DOCUMENTS

WO WO 2006/035199 4/2006

OTHER PUBLICATIONS

International Searching Authority; International Search Report and Written Opinion of the International Searching Authority; International Application No. PCT/US2015/029466; Patent Cooperation Treaty; pp. 1-10; publisher United States International Searching Authority; Published Alexandria, Virginia, US; copyright and dated Jul. 24, 2015; (9 pages).

(Continued)

*Primary Examiner* — Nay Tun
(74) *Attorney, Agent, or Firm* — Metz Lewis Brodman Must O'Keefe LLC (57) ABSTRACT

A detection system for identifying deterioration in a structure is provided that has acoustic sensors that receive acoustic emission waves. The acoustic emission wave detected by the acoustic sensor is identified as a hit. An analysis circuit is present that identifies an A state, a B state, and a C state. The B state has increased hit activity from the A state where a rate B is greater than a rate A by a factor of f1. The C state has increased hit activity from the B state where a rate C is greater than the rate A by a factor of f2. An alarm is activated when an amount of time that the C state is identified as being present reaches a value of TM, or alternatively when a threshold value based upon of the number of hits and time in the C state is reached.

21 Claims, 8 Drawing Sheets

Related U.S. Application Data (60) Provisional application No. 60/927,523, filed on May 4, 2007.

(51) Int. Cl.

| | |
|---|---|
| *G01H 1/00* | (2006.01) |
| *G01L 1/25* | (2006.01) |
| *G01M 5/00* | (2006.01) |
| *G08B 21/02* | (2006.01) |

(52) U.S. Cl.
CPC ........ *G01M 5/0041* (2013.01); *G01M 5/0066* (2013.01); *G01N 2291/105* (2013.01); *G08B 21/02* (2013.01)

(56) References Cited

U.S. PATENT DOCUMENTS

| | | | | |
|---|---|---|---|---|
| 4,152,929 | A * | 5/1979 | Edmond | G01L 1/255 |
| | | | | 73/581 |
| RE30,183 | E | 1/1980 | Popenoe | |
| 4,295,377 | A * | 10/1981 | Couchman | B25B 23/14 |
| | | | | 73/761 |
| 4,318,302 | A * | 3/1982 | Choi | E21C 39/00 |
| | | | | 73/579 |
| 4,322,193 | A | 3/1982 | Stahl | |
| 4,410,296 | A | 10/1983 | Unrug | |
| 4,601,207 | A | 7/1986 | Steblay | |
| 4,901,575 | A * | 2/1990 | Bohannan | G01H 1/00 |
| | | | | 73/587 |
| 5,205,176 | A | 4/1993 | Kibblewhite | |
| 5,220,839 | A | 6/1993 | Kibblewhite | |
| 5,329,465 | A * | 7/1994 | Arcella | G07C 3/00 |
| | | | | 137/554 |
| 5,345,684 | A | 9/1994 | Shoup | |
| 5,798,981 | A * | 8/1998 | Littlejohn | G01N 29/045 |
| | | | | 367/13 |
| 6,076,405 | A * | 6/2000 | Schoess | G01H 1/003 |
| | | | | 73/587 |
| 6,354,152 | B1 | 3/2002 | Herlik | |
| 6,399,939 | B1 * | 6/2002 | Sundaresan | G01H 1/12 |
| | | | | 250/231.1 |
| 6,418,384 | B1 * | 7/2002 | Rothea | G01D 1/18 |
| | | | | 702/56 |
| 6,507,790 | B1 | 1/2003 | Radomski | |
| 6,826,982 | B2 * | 12/2004 | O'Brien | G01M 5/0033 |
| | | | | 702/188 |
| 6,995,676 | B2 * | 2/2006 | Amacher | G08B 21/20 |
| | | | | 340/539.22 |
| 7,043,989 | B2 * | 5/2006 | Brink | E21D 20/02 |
| | | | | 73/579 |
| 7,080,555 | B2 * | 7/2006 | Austin | G01H 1/00 |
| | | | | 702/35 |
| 2003/0140701 | A1 * | 7/2003 | O'Brien | G01M 5/0033 |
| | | | | 73/596 |
| 2004/0035218 | A1 | 2/2004 | Paulson | |
| 2005/0017873 | A1 * | 1/2005 | Liu | G01M 5/0008 |
| | | | | 340/870.01 |
| 2008/0278319 | A1 | 11/2008 | Meiksin | |
| 2010/0107765 | A1 * | 5/2010 | Murakami | G01N 29/043 |
| | | | | 73/587 |
| 2010/0253490 | A1 * | 10/2010 | Sakai | G08B 13/1672 |
| | | | | 340/426.1 |
| 2012/0125108 | A1 * | 5/2012 | Muravin | G01N 29/043 |
| | | | | 73/587 |
| 2014/0123758 | A1 | 5/2014 | Gebski | |

OTHER PUBLICATIONS

"Reinforcement Analysis and Design of Mechanical Roof Bolting Systems in Horizontally Bedded Mine Roofs," H.Y. Tang and S.S. Peng, Geotechnical and Geological Engineering, vol. 3, No. 1, Mar. 1985; (parent U.S. Appl. No. 12/151,077).

"A New Concept for Roof Support," J.C. Stankus and S.S. Peng, Coal Magazine, Sep. 1996; (parent U.S. Appl. No. 12/151,077).

"Anchorage Pull Testing for Fully Grouted Roof Bolts," C. Mark, C.S. Compton, D.C. Oyler, and D.R. Dolinar, International Conference on Ground Control in Mining, Morgantown, WV, pp. 105-113, Aug. 2002; (parent U.S. Appl. No. 12/151,077).

"Investigation of Fully Grouted Roof Bolts Installed Under In Situ Conditions," C. Compton and D. Oyler, Proc. of the $24^{th}$ International Conference on Ground Control in Mining, Morgantown, WV, pp. 302-312, 2005; (parent U.S. Appl. No. 12/151,077).

"Roof Bolt Response to Shear Stress: Laboratory Analysis," E. McHugh, S. Singer, Proc. of the $18^{th}$ International Conference on Ground Control in Mining, Morgantown, WV, pp. 232-238, Aug. 1999; (parent U.S. Appl. No. 12/151,077).

Roof Monitoring in Limestone-Experience with the Roof Monitoring Safety System (RMSS), T.E. Marshall, L.J. Prosser, A.T. Iannacchione, M. Dunn, Proc. of the $19^{th}$ International Conference on Ground Control in Mining, Morgantown, WV, pp. 185-191, Jan. 2000; (7 pages).

"The Relationship of Roof Movement and Strata-Induced Microseismic Emissions to Roof Falls," A.T. Iannacchione, P.R. Coyle, L.J. Prosser, T.E. Marshall and J. Litsenberger, Minerals Engineering, vol. 56, No. 12, pp. 53-60, Dec. 2004; (parent U.S. Appl. No. 12/151,077).

"Characteristics of Mining-Induced Seismicity Associated with Roof Falls and Roof Caving Events," A.T. Iannacchione, G.S. Esterhuizen, T.S. Bajpayee, P.L. Swanson and M.C. Chapman, Proc. of the $40^{th}$ U.S. Rock Symposium, American Rock Mechanics Association, Anchorage, Alaska, pp. 1-10, Jun. 2005; (parent U.S. Appl. No. 12/151,077).

"Forecasting Roof Falls with Monitoring Technologies—A Look at the Moonee Colliery Experience," A.T. Iannacchione, T.S. Bajpayee and J.L. Edwards, Proc. of the $24^{th}$ International Conference on Ground Control in Mining, Morgantown, WV, pp. 44-51, Aug. 2005; (parent U.S. Appl. No. 12/151,077).

"Three Dimensional Microseismic Monitoring of a Utah Longwell," J.L. Ellenberger, K.A. Heasley, P.L. Swanson and J. Mercier, Rock Mechanics in National Interest, vol. II, pp. 1321-1326, Jul. 2001; (parent U.S. Appl. No. 12/151,077).

"An Analysis of Rock Failure Around a Deep Longwell Using Microseismics," K.A. Heasley, J.L. Ellenberger and P,.W. Jeran, $20^{th}$ International Conference on Ground Control in Mining, Morgantown, WV, pp. 280-286, Aug. 2001; (parent U.S. Appl. No. 12/151,077).

"Microseismic Activity Associated with a Deep Longwell Coal Mine," K.A. Heasley, J.L. Ellengerger and P.W. Jeran, SME Annual Meeting, Phoenix, AZ, preprint 02-175, pp. 1-5, Feb. 2002; (parent U.S. Appl. No. 12/151,077).

* cited by examiner

METHOD AND APPARATUS FOR DETECTION OF STRUCTURAL FAILURE

CROSS-REFERENCE TO RELATED APPLICATION

The present application is a continuation-in-part application of U.S. patent application Ser. No. 12/151,077 filed on May 3, 2008 that issued as U.S. Pat. No. 8,723,673 on May 13, 2014. U.S. patent application Ser. No. 12/151,077 claims benefit to U.S. Patent Application Ser. No. 60/927,523 filed on May 4, 2007. Both U.S. patent application Ser. No. 12/151,077 and 60/927,523 are incorporated by reference herein in their entireties for all purposes.

BACKGROUND OF THE INVENTION

Field of the Invention

The present invention relates to acoustic sensing and alarm methods and devices for affixing to support components of a structure. More specifically, the invention relates to a self-managed sensing and alarm system for continuous monitoring of infrastructure structural integrity and deterioration, particularly with respect to assembled structures such as bridges and integrated structures such as bolted support roofs in underground mines.

Description of the Prior Art

According to the Mine Safety and Health Administration, 1,500-2,000 reportable roof falls occur each year in underground coal mines in the United States. Roof fall is the primary cause of accidental deaths in underground mines, resulting in dozens of deaths and thousands of injuries every year. According to MSHA reports, 70% of all accidental deaths in underground mines are caused by roof fall. The average cost of such an incident is between $1.5 million and $3.5 million, with an annual cost to the industry in the billions of dollars in lost production, repair, and cleanup.

There are 590,000 highway bridges in the United States. Many of these bridges are aging, posing catastrophic danger to human life in light of the undetected or underdetected impending failures or corrosion of structural components. The present state of the art for the assessment of structural health of bridges depends primarily on visual inspection that can recognize damage only in a late state of deterioration.

Figure 1A:
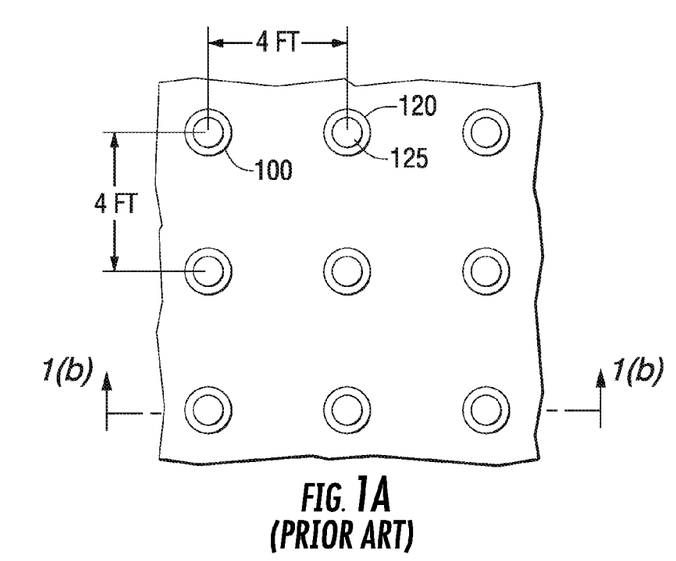
FIG. 1A is a diagrammatic plan view of an underground mine roof bolt arrangement of the prior art.
Figure 1B:
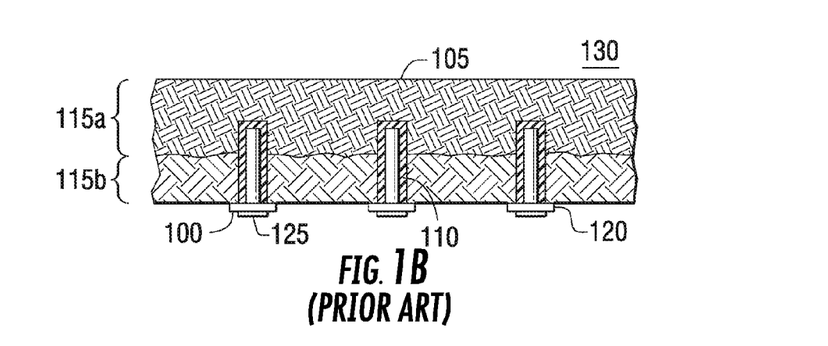
FIG. 1B is a sectional view of the roof bolts of FIG. 1A taken along line I(b)-I(b).

Referring to FIG. 1A, roof bolts 100 are typically placed four feet apart in order to create support roofs in underground mines. The roof bolts 100 are anchored in the roof 105, as shown in FIG. 1B, utilizing a settable resin 110 around the bolt and are tightened to hold the various strata 115a, b of the roof 105 together. Less common is the use of an expandable mechanical anchor for anchorage. In either case, support is provided by the tensile load imparted to each bolt upon tightening the bolt head into tight abutment with the mine roof through a mounting plate 120 positioned between the mine roof 105 and the bolt head 125.

Figure 1C:
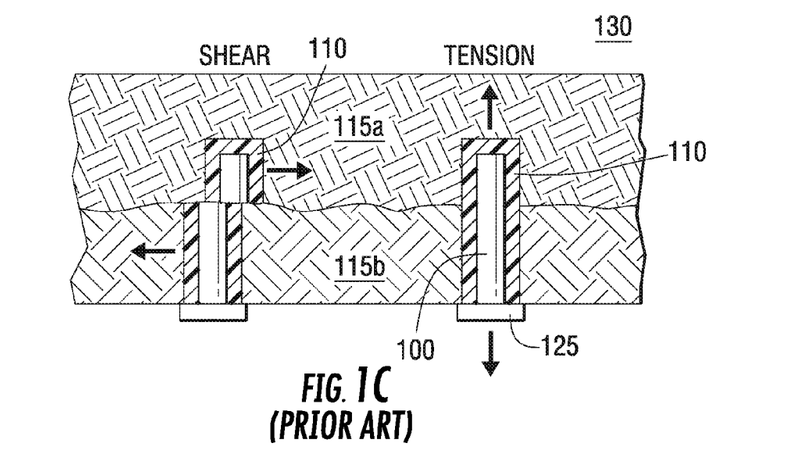
FIG. 1C is a prior art sectional view of roof bolts under stress.

A number of prior art methods have been utilized to study and increase beam strength and improve roof support. Nevertheless, in time as mining continues, the strata 115 may start to separate and develop a tensile load on the bolt, as shown in FIG. 1C. A layer of the strata may also shift horizontally exerting shear stress on the bolt. These forces can result in three different conditions causing roof collapse: (1) the bolt anchorage may fail causing the bolt to slide out of its position, (2) the bolt may fail and eventually break and (3) the roof may crack or separate above the layers held in place by the bolts, known in the art as a cutter roof failure. Statistically, the probability of roof falls in a given mine is 2.5 per year.

Figure 2:
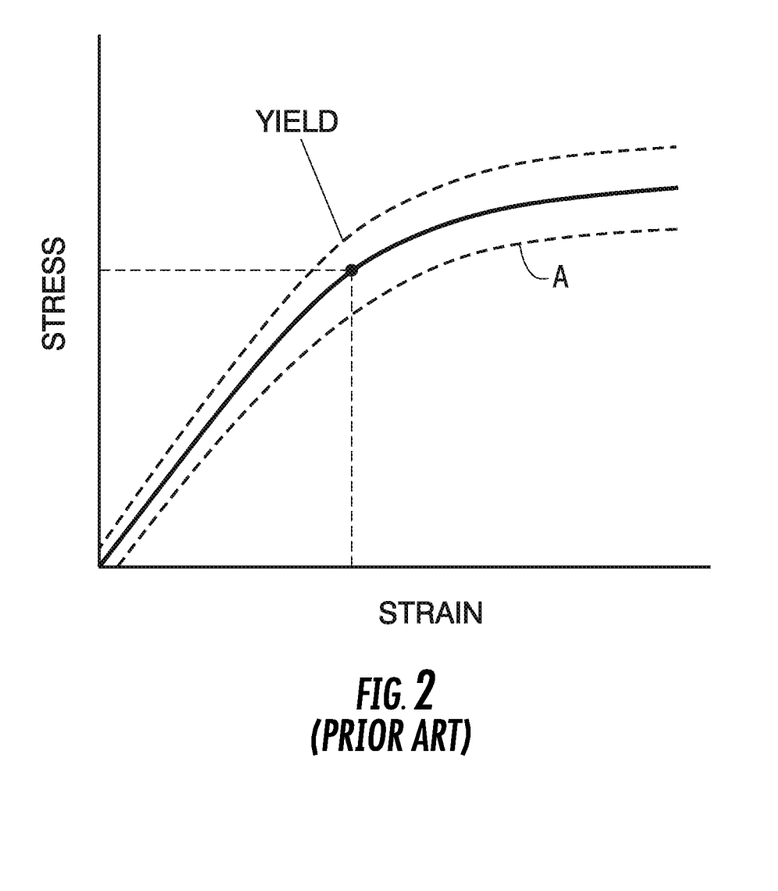
FIG. 2 is a diagrammatic view of a stress/strain graph of a roof bolt of the prior art.

Past efforts to predict roof fall have not yielded viable results. A number of prior art references based on bolt loading, tension or strain measurements address the stress-strain relationship in materials. Generally, referring to FIG. 2, as the bolt is loaded or stressed, i.e., put under tension by weight of the overburden 130, typically clay, rock, coal or sand above the mine passage or tunnel, the bolt is strained, i.e., elongated. As shown in FIG. 2, when a critical stress and corresponding strain are reached, the bolt enters the yield region after which it breaks. One prior art approach was to measure the stress or strain, allowing impending bolt breakage to be detected. Experience in the field has shown that these methods are unreliable. Sometimes they predict bolt breakage when the bolt does not break, and at other times they do not predict bolt breakage when bolts do break.

The reason for this failure to predict bolt breakage is inherent in the variable monitored. Not all nominally identical bolts, i.e. identical model number, are in fact identical. The material from which a given batch of bolts is manufactured is not perfectly uniform. There will be certain variations from bolt to bolt. Manufacturing dimension tolerances compound these variations and the unpredictability. Consequently, the stress-strain curves for a given bolt model, in practice, display a spread as shown by area A in FIG. 2. Furthermore, the stress-strain curves for a given single bolt are different for different applied stress histories. In a mine roof, for example, if the bolt is stressed gradually over a long period of time, the curve will be different from a curve associated with spurts of stress over the same period of time, and still different from a curve associated with the same stress levels applied over a different period of time.

Most of the prior art is directed toward the measurement of load, strain or tension on the bolt, and several include the generation of a signal by the measuring device which is propagated within the bolt and the subsequent detection of changes to that signal over time, such as such as Spengler, et al., U.S. Pat. No. 4,149,446, issued Apr. 17, 1979 Popenoe, U.S. Pat. No. 4,114,428, issued Sep. 19, 1978; Choi, U.S. Pat. No. 4,318,302, issued Mar. 9, 1982 and Kibblewhite, U.S. Pat. No. 5,205,176, issued Apr. 27, 1993. Furthermore, the strain in a bolt in response to applied stress is different at different locations along the bolt. While the strain in a bolt is still in the safe zone at one location in the bolt, it may already be at the yield point at another location in the bolt. Installing multiple strain sensors on each bolt would make the system too expensive and measuring strain everywhere along the bolt is entirely impractical. Furthermore, strain data does not necessarily provide the needed information. Shear loading also contributes significantly to bolt failure in roof support in mines, which is not considered at all in load or strain measurements that use load cells, pressure sensitive discs or strain gages.

A different approach to predict roof fall addresses the measurement of roof sagging. Extensometers are used to determine the magnitude, position and rate of movement of soil or rock surrounding an excavation. They are widely used in mining to obtain support design information and as the basis of safety monitoring systems. Extensometers are installed into boreholes and, in mining, the smaller the diameter the better to minimize drilling costs. The simplest form of extensometer makes use of a stainless steel spring reference anchor with a tube indicator attached to it by stainless steel wire and visible at the hole mouth. Movement is indicated by colored reflective bands on the indicator, which are progressively covered as movement develops. In mining, a simple extensometer such as this is known as a "telltale" because it gives a visual indication of roof movement. A large number of such devices would have to be installed to cover a single mine. The National Institute of Occupational Safety and Health developed a Roof Monitoring Safety System that measures roof movement intended for use in wide-open roofs such as in room-and-pillar stone mines. NIOSH admits that this system is not suitable to predict roof fall.

Field use has shown that prediction based on telltale devices is unreliable. Roofs do collapse without prior indication from the device, and sometimes the device indicates an alert to an impending roof fall when the roof keeps staying intact. The failure of the telltale to forecast roof falls is rooted in the quantity that is being measured, i.e., roof sagging. The instrument measures by how much the roof at a given location has sagged relative to a reference point. The reference point is the anchorage location of the instrument that is assumed not to change, a questionable assumption, and furthermore, the instrument does not measure by how much the strata or the structure that holds the strata together has actually weakened.

Sagging of the mine roof results in vertical and horizontal stresses, imparting both axial and shear forces on the roof bolts. Combined tensile and shear forces are at times sufficiently large to cause bolt failure. Whether a bolt fails or not depends on the bolt material, structure and dimensions, on the anchorage resin, on the surrounding rock quality and on the angle between the bolt axis and the direction of the boundary between strata layers. None of these factors are considered or evaluated using the telltale instrument measurements. Therefore, the degree of roof sagging is not a measure of the structural state of the roof and the instrument does not reliably predict roof collapse. Although the strata may have shifted, the structure of the anchored bolts that support the strata may still be perfectly capable of holding the strata together. Alternatively, while roof lowering may be relatively small, the separation between the particular strata may have reached a critical value or the bolt structure that holds the roof together may have weakened to a critical level.

Other prior art methods of detection are based on studies of micro-seismic emission, which deploy geophones over mine roof areas. The geophones upper frequency limit ranges between 4.5 and 14 Hz. High frequencies on the order of hundreds or thousands of kilohertz cannot be detected over large areas because of severe attenuation of high frequency pressure or sound waves. Such systems require the installation of geophones in boreholes in mines and moving or adding them into new boreholes as mining advances. Under this system, in order to determine whether a roof fall is imminent, and its location, it is necessary to combine four computed parameters and apply human interpretation. To date these seismographic studies are unable to reliably predict roof fall. Two problems associated with this approach are that high frequencies cannot be detected and that location determination depends on the speeds of sound wave propagation in various directions. These speeds are not reliably predictable, as they depend on the rock strata's non-homogeneous structures.

In summary, while the need to be able to predict impending roof fall in underground mines or other structural failure in rigid support structures, such as bridges, in time to be able to take proactive action to prevent failure and related injuries is lacking in the art. A system is necessary to identify an alarm condition in time to take proactive action to prevent failure.

SUMMARY OF THE INVENTION

A system is disclosed which places sensors at strategic positions on a given infrastructure and provides an alert alarm when the structure reaches a weakened structural state that requires taking proactive action to prevent infrastructure collapse. The system can be applied to, among other structures, roofs in underground mines and highway bridges. In underground mines, for example, one sensor is preferably placed on each targeted roof bolt head but may be installed on a more limited number of roof bolt heads. When the infrastructure or component weakening reaches a critical level, an alarm, such as a sonic alarm, visible indication, or communication warning, such as a page or computer alert is activated. This may be accomplished by direct electrical connection, an electronic signal which is broadcast by a transmitter sending an alarm signal to a display in a maintenance office or through a communications network such as the Internet. Alternatively, the alarm condition may be stored in a memory and extracted upon demand by a receiver device such as in a passive RFID system. As would be apparent to one skilled in the art, any conventional warning or notification system may be utilized.

The sensors preferably utilized in this system respond to acoustic emission, or AE pressure waves from the target metallic material, anchorage resin or overburden, i.e. the surrounding matrix, transmitted through the target metallic material acting as an acoustic waveguide. Conventional AE sensors are typically manufactured of piezoelectric crystals and are associated with a high cost of acquisition and operation. The present system may preferably utilize a much lower cost sensor manufactured of piezoelectric films.

In bridges, sensors can be placed to sense AE transmitted through embedded bolts or steel cables. The signals may, for example, be transmitted by micro-transmitters to a central transceiver installed on the bridge and the central transceiver can transmit the signal by a communications network such as the internet to a computer at a maintenance office or other monitoring station. The sensors and associated electronics may, in order to be cost effective, be energized by solar cells.

When material such as metal, concrete or rock is stressed, it emits acoustic waves generally within a frequency range between tens of kilohertz and a few megahertz. These pressure waves originate from atomic dislocations and micro-cracks as well from cracks propagating into macro-cracks. The waves may be characterized and identified by selection and combination of predictable parameters such as amplitude, frequency, energy, duration and rate of occurrence. As the material approaches a critical zone, such as yield, the rate of AE occurrence increases dramatically.

Many infrastructures contain metal imbedded in other material. As stated earlier, miners install roof bolts of lengths generally between five and twenty feet long, typically in a four feet-by-four feet grid. In pre-stressed concrete highway bridges, reinforcing rods and steel cables are embedded in concrete.

One embodiment of the disclosed system is applied to roof bolts which tie mine roof layers together. Sensors attached to roof bolts detect acoustic emission originating in the bolts, resin, or overburden around and above the bolts. When a critical level of structural deficiency has been reached, the sensor module activates an alarm condition. As referred to in this application, an acoustic wave detected by a sensor and identified as a significant event is called a hit. A critical level of events, or alarm condition, is determined when the hit rate increases dramatically, preferably beyond a preset threshold parameter, e.g., by a factor of 8. Such a rate change indicates that the bolt, surrounding anchorage or overburden has reached a critically weakened point. The sensor converts the pressure wave to a voltage that is processed by an electronic circuit. In the preferred embodiment, the voltage waveforms that represent the pressure waves or hits, are envelope-detected and the number of envelopes per given time interval are counted and a sensor output value is computed. This is preferably the ratio between the measured or detected number of hits for a particular time interval and a baseline reference value, entered in memory. The baseline reference value is an average obtained over an initial, preset time period when the bolt is first installed. The detection of any of these conditions causes the hit rate to increase at a rate beyond a preset threshold and an alarm condition is identified.

Examples of alarm indicators are visible indicators, such as LEDs that turn on or an RF transmitter that emits a warning signal. In practice, a situation that requires immediate action may be defined based on patterns associated with the alarm indicators. For example, a single lit LED may not cause concern because the roof weight may be taken up by neighboring bolts. Similarly two lit LEDs several neighbors apart may not be of concern. On the other hand, three immediate neighboring lit LEDs, for example, may require immediate action to prevent roof collapse.

When RF transmitters are used, they may communicate with the mine communications network, and be transmitted, for example, to the maintenance crew office below or above ground and a pattern can be displayed on a video terminal. Algorithms which include preset thresholds for the various parameters allow a computer to automatically determine whether immediate action is needed or not.

Some distinguishing properties of this system are: (1) the location of the infrastructure weakening area is not determined by a triangulation technique and human judgment, but directly by the sensor location indicated by an LED or video monitor; (2) the infrastructure weakening is not measured in terms of "typical" or "average" values that miss alarm states, or cause false alarms, but the measurement is self referenced; and (3) the film sensors are very inexpensive relative to traditional sensors.

These and other advantages and features of the present invention will be more fully understood upon reference to the presently preferred embodiments thereof and to the appended drawings.

DETAILED DESCRIPTION OF THE PREFERRED EMBODIMENTS

Figure 3A:
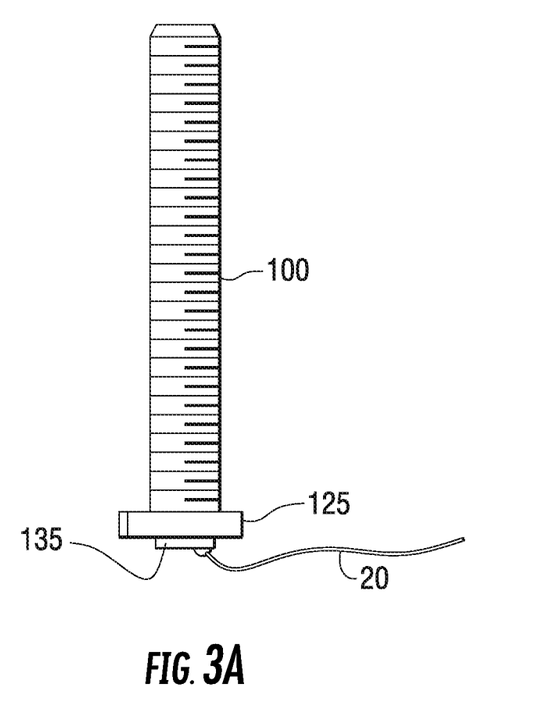
FIG. 3A is a side view of a roof bolt having a sensor of the present invention mounted thereon.
Figure 3B:
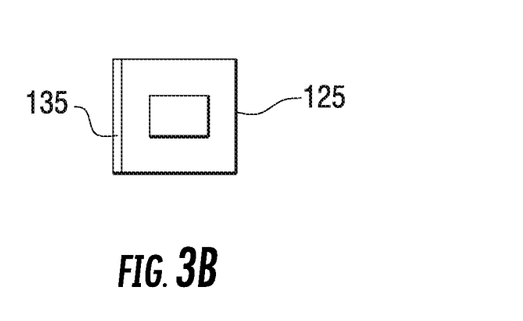
FIG. 3B is a top plan view of a roof bolt having a sensor of the present invention mounted thereon.
Figure 4:
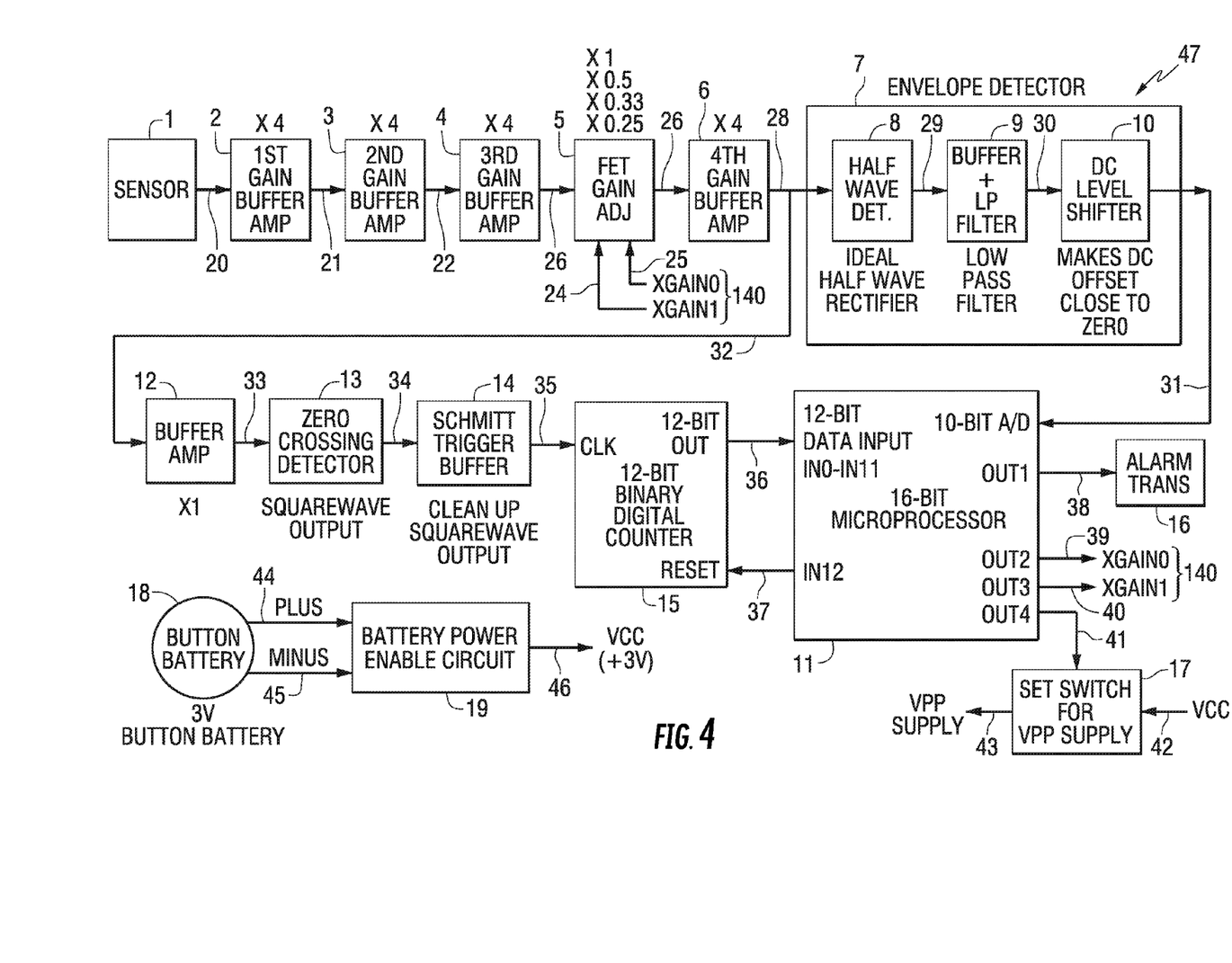
FIG. 4 is a diagrammatic view of the electronic circuitry of one embodiment of the present invention.

Referring now to FIGS. 3A, 3B and 4, one embodiment of the system 47 illustrates a sensor device 135 attached to the head 125 of a roof bolt 100. The sensor device 135 may contain an AE sensor 1 alone, together with a transmitter (not shown) for wireless communication to the remainder of the system, a sensor lead 20 for wired electronic communication to the remainder of the system, or may contain the entire system in a discrete housing. The AE sensor 1 may be constructed of a piezo film sensor such as the LDTO-028K/L sensor, manufactured by Measurement Specialties, Inc.

Referring now to FIG. 4, sensor 1 sends the output signal through sensor line 20 to buffer amplifier 2. The buffer stage is desirable because the sensor has high output impedance. Buffering the output makes the signal less susceptible to noise. The buffered signal is transmitted through line 21 to amplifier 3. The output signal from amplifier 3 is transmitted through line 22 to amplifier 4 where it is further amplified. The signal is then sent through line 26 to an automatic gain control amplifier 6. The gain is controlled through gain input signals 140 entering AGC amplifier 6 through lines 24 and 25. The gain input signals 140 for AGC amplifier 6 are transmitted from microprocessor 11 through lines 39 and 40 to FET gain adjustment circuit 5. The microprocessor 11 adjusts the gain for AGC amplifier 6 based on the envelope amplitude that it detects through line 31 from the output of envelope detector circuit 7, as will be described below. The envelope detector circuit 7 consists of half wave rectifier 8, buffer and low pass filter 9, and DC level shifter 10. The output from FET gain adjustment circuit 5 feeds into amplifier 6 through line 26. AGC amplifier 6 sends its output signal through line 28 to buffer and low pass filter 9 through line 29. The output of buffer and low pass filter 9 send its output signal through line 30 to DC level shifter 10. The DC level shifter is used so that the envelope detector circuit 7 output is read by microprocessor 11 only if the envelope detector circuit 7 output signal is above a certain threshold, for example 0.2 volts. This is needed in order not to mistake noise for signal. Prior to entering DC level shifter 10, the signal has an offset of one half of the battery voltage because of the use of a single battery supply. Level shifter 10 adjusts the threshold level to the desired value.

AGC amplifier 6 sends its output signal also to buffer amplifier 12 through line 32. The output from buffer amplifier 12 enters zero crossing detector 13 through line 33. Each zero crossing of the output signal from AGC amplifier 6 triggers Schmitt trigger buffer through line 34. Schmitt trigger buffer 14 connects to digital counter 15 through line 35 causing digital counter 15 to count the number of zero crossings of the signal coming from the output of AGC amplifier 6. The count in digital counter 15 is transmitted to microprocessor 11 through line 36. When digital counter 15 reaches a predetermined value, a signal is output through line 37 from microprocessor 11 to reset the digital counter 15.

As is clear from the description above, signal waveform output of sensor 1 can be closely reproduced from the envelope and zero crossing information in microprocessor 11. How the information is used will become clear with reference to FIG. 5 and its associated description, below.

To preserve battery energy, the system may be put at certain times, to be defined below, into an inactive or sleep mode. This is controlled by microprocessor 11 through line 41 that connects to inactive mode switch 17. When inactive mode switch 17 is closed, battery voltage VCC is applied as the supply voltage VPP to system 47. Battery 18 has its positive and negative terminals connected, respectively, through lines 44 and 45 to battery power enable circuit 19. This prevents battery 18 from excessive discharge when system 47 is not in use. Battery power enable circuit 19 is enabled when system 47 is made ready for use. When battery power enable circuit 19 is enabled, the output voltage of battery 18 is applied to system 47 through line 46.

In operation, microprocessor 11 receives signal information originating in acoustic sensor 1. The information received includes envelopes of the acoustic signal, which are typically in the 600 μs to 2 ms range and threshold crossings of the acoustic signal. Based on this information, microprocessor 11 determines when an alarm condition has been reached as will be illustrated further with respect to FIG. 5. In addition, microprocessor 11 performs power management functions so that maximum battery life is achieved. System 47 will be placed in an inactive mode much of the time. Periodically, dependent on the detected acoustic emission activity in the previous active mode, system 47 will resume function, take readings, determine if alarm conditions are present and, if appropriate, return to the sleep mode as will be illustrated with reference to FIGS. 5 and 6, below. System 47 may include alternative embodiments without changing its essential functioning. For example, buffer amplifiers 2, 3 and 4 can be replaced with a single amplifier. Three amplifiers are preferably used to obtain both high gain and broad bandwidth. Obtaining the same features in a single amplifier is much more expensive and causes much higher energy use causing quicker battery drain. As another example, the zero crossing count in microprocessor 11 can be used to separate output signals, e.g., of 300 kHz from signals of 700 kHz. Similar information can be obtained by inserting two band-pass filters in parallel, before the input to envelope detector circuit 7. Band-pass filters may be employed to reduce the amount of electromagnetic information which must be processed. For example, a first, or low frequency range band pass filter between 100 kHz and 300 kHz and a second, or high frequency range band pass filter between 350 kHz and 700 kHz may be applied to filter the voltage coming from the sensor output. Output signal from both frequency ranges indicate that AE is coming from the bolt itself. An output signal from only the low frequency range indicates that the bolt anchorage has weakened either because the anchorage resin has deteriorated to a critical level, or the overburden has cracked to a critical level.

Figure 5:
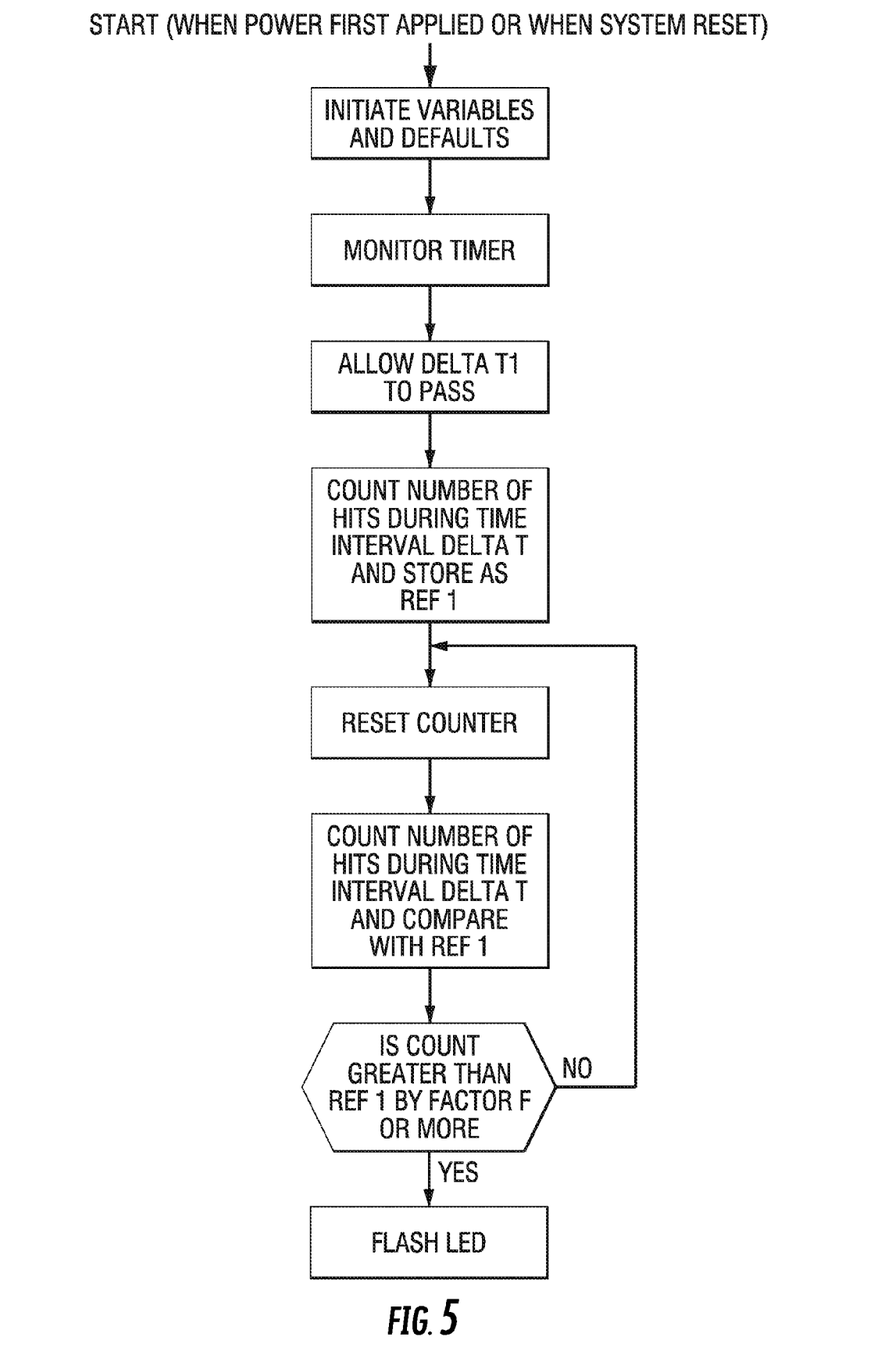
FIG. 5 is a diagrammatic view of a decision tree illustrating a first embodiment of the logic of the electronic circuitry of the present invention.
Figure 7:
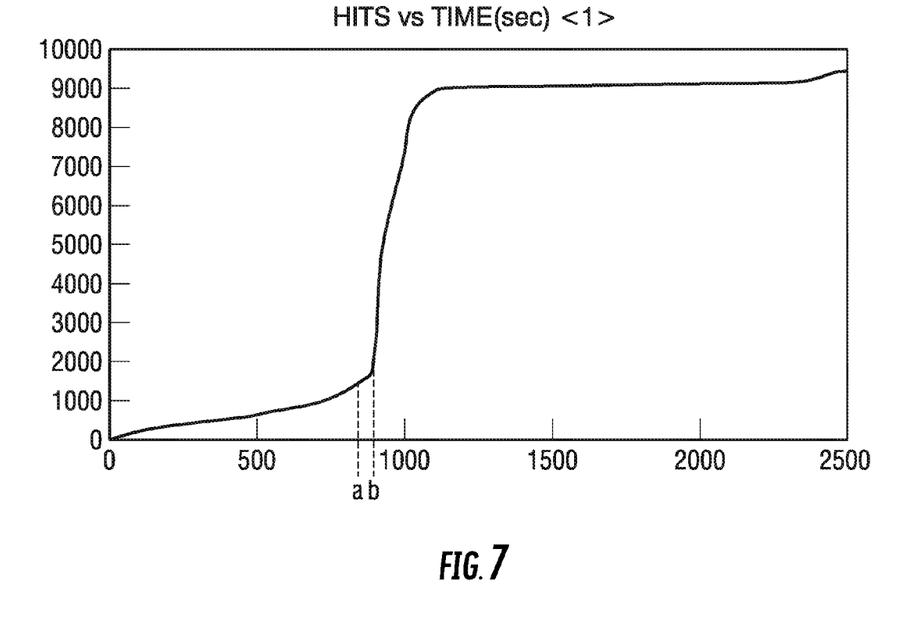
FIG. 7 is a graph view of the calculation of the sensor output value over time.

Several different embodiments may be implemented in terms of procedures as expressed by way of software and executed by microprocessor 11. FIG. 5 illustrates the preferred methodology. When power is first turned on for system 47, the variable and default values of microprocessor 11 are initiated including setting values for DELTA T1, DELTA T and threshold variable F. A time period DELTA T1 is allowed for the system that is being monitored to settle before the acoustic emission hit count is detected. In a mine roof embodiment, for example, when a roof bolt is first installed in the roof, it takes time for the roof bolt and resin structure to settle in the rock strata, causing unique acoustic emission signals during this transition period. After period DELTA T1 has elapsed, the number of hits during a time interval DELTA T is counted and stored in memory as variable REF 1. This establishes the baseline reference value for all further measurements. In the mine roof embodiment, a baseline is established for each particular bolt in the roof structure. The counter is reset and a new count of hits during each time period DELTA T is made. The number of counts is compared with the value REF 1 for each time period DELTA T to create a sensor output value curve, as shown in FIG. 7, which may be a rate ratio, a frequency measurement or other calculated value as identified elsewhere in this application. FIG. 7 is a graph of hit values against time and particularly illustrates a bolt being exposed to increasing stress. The graph line undergoes a significant shift in slope between points a and b and the ratio of measured hits to the baseline value within this range exceeds the threshold of 8, set as REF 1. When the count is less than the value REF 1 by a preferred factor of 8, then the counter is reset after which a new hit count is begun. If the count is greater than the value REF 1 by a factor of 8 or more, then an alarm condition is identified and an alarm signal is transmitted to the users through line 38, as shown in FIG. 4 to alarm/transmitter 16. This may be by a visual indicator such as a flashing LED. Alternatively, the device may transmit an alarm signal through a transmitter well known to those skilled in the art to a remote location where the alarm would be sounded or displayed. The alarm condition is identified and an alarm signal is generated when the object being monitored has reached a significant degree of weakening. In the roof bolt example, the material yield point would have been reached.

In this example, comparing the number of hits counted during a fixed time interval with a reference value identified the alarm condition. Another way to identify the alarm condition is to take the derivative of the cumulative hit count. Under safe conditions, the slope of the cumulative hit curve, when plotted, has a nearly constant slope. When the yield zone of material is entered the slope increases dramatically and soon reaches a new, higher, nearly constant slope. Microprocessor 11 can thus compute the derivative of the cumulative hit count and determine the alarm level when the derivative increases by a factor of five, for example. To avoid errors caused by minor fluctuation in slope, the derivative can be averaged over short periods of time.

In an alternative embodiment, the signal frequency of each hit can be monitored. A shift from a high frequency content of 600 kHz, for example, to a low frequency content of 300 kHz, for example, would indicate that the anchorage or strata around the bolt has weakened to a degree that identifies an alarm condition. This can be accomplished by inserting two band-pass filters in system 47, or by monitoring the threshold cross over in microprocessor 11 as described above. Alternatively, the hit rate and the frequency of the acoustic emission can be monitored and the OR function can be utilized to identify an alarm condition when either of these measurements indicate that the danger zone has been entered.

Figure 6:
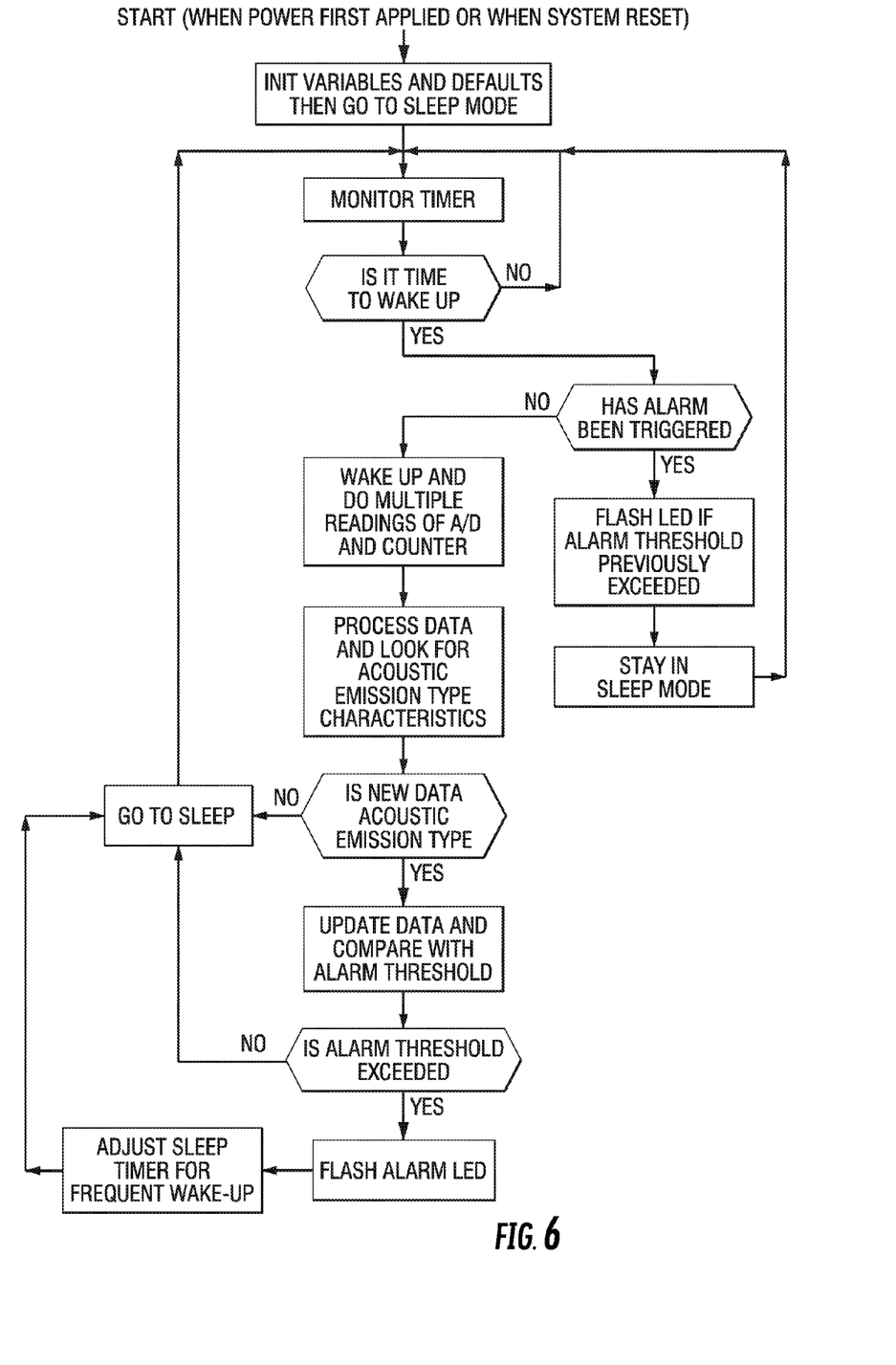
FIG. 6 is a diagrammatic view of a decision tree illustrating a second embodiment of the logic of the electronic circuitry of the present invention.

FIG. 6 illustrates an embodiment of an energy saving mode. System 47 is fully powered up only at certain time intervals during which periods readings are taken. In order not to miss important events, the inactive period length is adaptable and varies dependent on values obtained when the last readings were taken. When the readings are benign, the inactive period is set for a longer interval. When the readings show a high degree of variability of data input or signals detected, the inactive period is set for a shorter interval. The program expressed by the flow chart of FIG. 6 includes a second energy saving feature. Instead of having an alarm signal, such as an LED flash, be transmitted continuously after an alarm condition has been detected, the alarm signal is discontinued turns off after one or several preset cycles and the timer is set for frequent wake up. In the following cycle, when the decision box HAS ALARM BEEN TRIGGERED, the output will be "YES" and the alarm signal, such as the LED flash is triggered again and the system goes back to inactive mode and the system goes back to the MONITOR TIMER box. After an alarm has been activated once, the cycling path is much shorter than the cycling path taken before an alarm condition was indicated, saving even more energy.

Another feature of embodiment illustrated in FIG. 6 is the box PROCESS DATA AND LOOK FOR ACOUSTIC EMISSION TYPE CHARACTERISTICS. Using signal envelope and threshold cross over information and comparison with previous reading results, the program will determine if the signal actually caused by acoustic emission. This step is particularly useful if the environment is very noisy. Persons skilled in the art, can easily add features such as low-battery indicator and certain LED flashing patterns to indicate that system status.

Information Added in Continuation-in-Part Patent Application

Infrastructure 105 such as an underground mine roof, highway bridge, or other structure experiences structural change from time to time. This structural change causes a pressure, wave in all directions from the location where the change takes place. As stated, this phenomenon is known as an acoustic emission event (AE event) and when sensed by an AE sensor may be known as an AE hit. The stability of the infrastructure 105 can be evaluated based upon the rate of AE hits that occur in the infrastructure 105 per unit of time. Different phases of stability of the infrastructure 105 can be defined in terms of their rate of AE hits.

A stability phase known as the A state 200 may exist where the infrastructure 105 experiences a nearly constant rate of AE hits and thus represents normal, stable activity. This A state 200 may also be said to represent the AE hit rate within the bolts 100 and surrounding strata 115*a*, 115*b*. The A state 200 may be the phase of acoustic activity in which normal background emissions are heard by the AE sensors 1, and may be a learning stage of the system 47 in which the AE sensors 1 establish the normal stable background AE hit rate of the particular infrastructure 105. The A state 200 may be the period of time DELTA T after DELTA T1 has elapsed as previously discussed in which the system is allowed to settle down after bolt 100 installation. The A state 200 may have a number of hits per given time interval that is defined as a rate A. Rate A may be different for different locations of the same infrastructure 105, and may be different from site to site.

Figure 8:
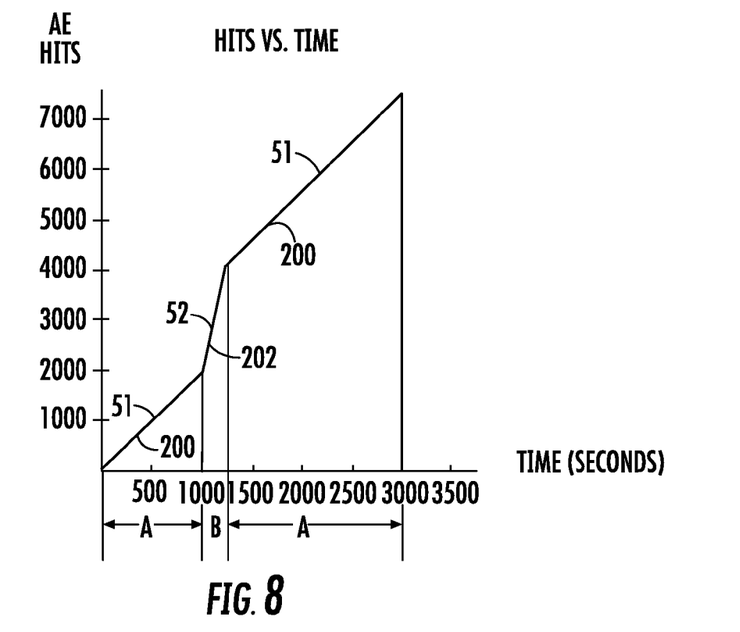
FIG. 8 is a graph of cumulative AE hits versus time for a system that detects an A state then B state followed by a second A state.

With reference to FIG. 8, a plot of the cumulative number of AE hits on the y-axis versus time on the x-axis for a given infrastructure 105 is displayed. The infrastructure 105 is shown as being in the A state 200 from time 0 seconds to time 1000 seconds. The A state 200 is characterized by a rate A that has a relatively small slope S1 that is stable. The line can be an actual line, or one that is formed through interpolation or averaging of various data points. The rate A may be a background rate as registered by the detection system 47, or may otherwise represent a stable condition of the infrastructure 105 and bolts 100 and their surrounding strata 115*a*, 115*b*. The analysis circuit of the system 47 may obtain data from the AE sensors 1, or the detection circuit of the system 47 may obtain signals from the AE sensors 1 and transfer this data to the analysis circuit so that the analysis circuit can identify the infrastructure 105 as being in the A state 200. The slope S1 may be 2 in accordance with one exemplary embodiment, and the rate A may be 2 hits per second. The rate A can be other rates in other exemplary embodiments such as 2.5 hits per second, 3 hits per second, 3.5 hits per second, 0-4 hits per second, or up to 5 hits per second in accordance with other exemplary embodiments.

Changes in the strata 115*a*, 115*b* or other portion of the infrastructure 105 may cause the rate of AE hits to climb over that of the rate A or the range of rate A defined for the A state 200. The analysis circuit will now identify the infrastructure 105 as being in a B state 202. The increased rate of AE activity may indicate that the infrastructure 105 is becoming more unstable and thus the system 47 may sound an alert to the user to indicate same. The system 47 may identify the B state 202 when the number of AE events in the given time interval increases by a factor f1 that can be in the range between fL and fH relative to the rate A in A state 200. For example, in one embodiment fL is 3 and fH is 6. As such, f1 may be in the range of 3-6 higher than rate A. In other arrangements, fL may be 4 and fH may be 9 such that f1 is in the range of 4-9. With reference to FIG. 8, the system 47 identifies a B state 202 from 1000 seconds to 1250 seconds. The number of cumulative hits in this time period is 2000, and the rate f1 is 8. If the system 47 is set up so that the fL to fH range is 4-9, the system 47 will identify the infrastructure 105 as being in the B state 202 when the rate f1 is 8.

The slope of the line in the B state 202 is S2 which is higher than the slope S1 when in the A state 200. The line in the B state 202 can be the actual measured values when in the equivalent time span, here 1000 seconds to 1250 seconds, or may be formed through a mathematical process such as interpolation. The lines may be generated the same way along all times in the graph, or different means of line generation may be performed in accordance with other exemplary embodiments. A visible and/or audible alert may be generated when the B state 202 is identified as being present to warn an operator that the infrastructure 105 is experiencing a higher than normal state of instability. This higher state of instability may settle down back to a lower rate of AE hits through normal processes inside of the earth or infrastructure 105. If a warning were to be delivered to the operator when in the B state 202 it may be premature or not even proper because the infrastructure 105 is not in danger of collapse or other failure.

This situation is shown in FIG. 8 in which the B state 202 is exited at time 1250 seconds and the system 47 begins to identify a lower rate of AE hit emission from the infrastructure 105 or bolts 100 or their surrounding strata 115*a*, 115*b*. The system 47 begins to identify the A state 200 at this point in time, and the slope of the line again becomes S1 which is 2 and the hit rate is 2 hits per second. Although this is the same as it was in the previous A state 200 from 0-1000 seconds, it may be different than this time period in other studies so long as it is below the set fL threshold that demarcates the difference between the A state 200 and the B state 202. As the infrastructure 105 has returned back to the A state 200 and is no longer in the B state 202, the alert that was generated may be stopped and the user no longer alerted to this heightened state of instability.

Figure 9:
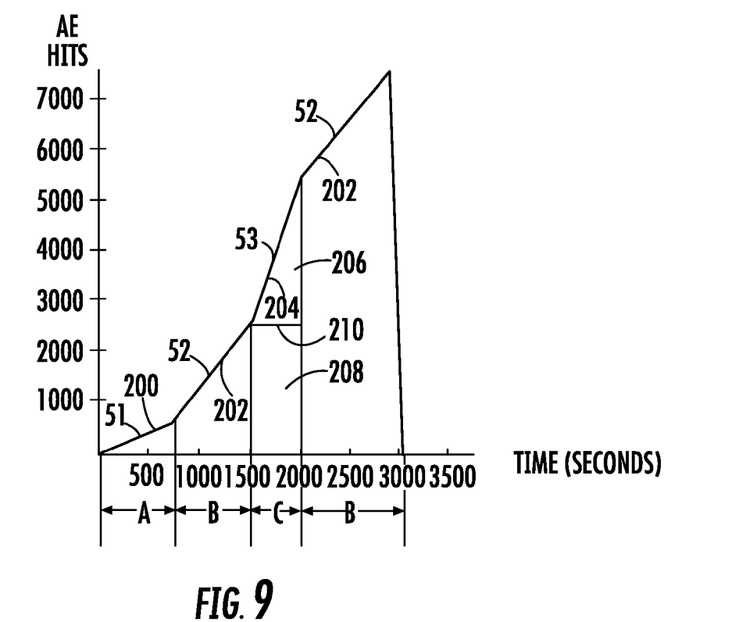
FIG. 9 is a graph of cumulative AE hits versus time for a system that detects an A state, then a B state, then a C state, then a second B state.

With reference now to FIG. 9, a second analysis of the infrastructure 105 using the system 47 is displayed. From 0-750 seconds the system 47 identifies the A state 200, and from 750-1500 seconds the B state 202 is identified. The alert may be given as previously stated when the B state 202 is identified. However, instead of settling back down into the A state 200 after being in the B state 202, the infrastructure 105 enters a state of even greater AE hit activity which may be referred to as a "catastrophic" state or C state 204. If this C state 204 is sustained collapse or other failure of the infrastructure 105 will result. The C state 204 is identified when the AE hit rate is a factor of f2, which is greater than f1, greater than the rate A. The AE hit rate ratio in the C state 204 may be a rate C that is greater than rate A by the factor of f2. The rate C may be greater than fH as previously mentioned. For example, if the range fL-fH is 3-6, then once rate C is greater than 6 the system 47 will identify the C state 204 as being present. The slope of the line in the C state 204 may be S3 and this slope is greater than S2 and is greater than S1.

The fH value may be different in accordance with other exemplary embodiments, and the fL value may likewise be different. In other arrangements, the fL-fH range may be 0.5-2, 1-2, 2-3, 2-5, 3-5, 4-5, 5-10, 1-15, or 3.5-10.

Once the infrastructure 105 enters the C state 204 of instability, the alert given in the B state 202 may continue or may cease. However, an alarm may be given when the system 47 identifies the C state 204 as being present. The alarm may be as previously described and is a more urgent notification to the user that the instability in the infrastructure is more serious and critical than when the alert is given. The system 47 may be arranged so that the alert is given immediately upon detection of the C state 204, or the system 47 can be set up so that the alert is not given upon immediate detection of the C state 204 but based upon a certain further event as being identified. These further events may be described as alarm initiation events that cause the alarm to generate when the system 47 identifies the C state 204 as being present above and beyond the simple identification of the C state 204 as being present.

The first alarm initiation event may be a measurement of the time that the infrastructure 105 is in the C state 204 after first being identified as being in the C state 204. It may be the case that certain structural adjustments are made to the infrastructure 105 that cause it to exit the C state 204 and reenter the B state 202 or even the A state 200. If this is the case, the infrastructure 105 is no longer in fear of collapse or other structural failure and there is no reason to give an alarm. If an alarm were given it would be a false alarm which would tie up resources and cause the user to tend to ignore future alarms because he or she would think that they were as well false alarms. The system 47 may monitor the amount of time that the C state 204 is identified as being present once the C state 204 is first identified as being present. As shown in the graph of FIG. 9, the C state 204 starts at 1500 seconds and ends at 2000 seconds and is thus 500 seconds in length. The system 47 may have a set value of TM which when reached causes the alarm to activate. In some arrangements, TM is 5 seconds. If the C state 204 is identified as being present for 5 seconds then the alarm is generated. If the C state 204 exits and the system 47 then identifies the B state 202 or A state 200 as being present before 5 seconds are reached, the alarm is not activated. Although described as being 5 seconds, the time TM may be 10 seconds, 15 seconds, from 20-100 seconds, from 100-500 seconds, or up to 1000 seconds in accordance with various exemplary embodiments.

Once the C state 204 is no longer identified and the infrastructure 105 returns to the B state 202 or the A state 200, the counter that measures the time in the C state 204 may be reset. In this regard, if TM were 5 seconds and the C state 204 lasted for 2 seconds, and subsequent reentry into the C state 204 was identified it would still be the case that 5 seconds of subsequent reentry into the C state 204 is required to sound the alarm. However, the system 47 can be alternatively configured in this regard. For example, if TM were 5 seconds and 2 seconds of time in the C state 204 were identified before the C state 204 was exited, subsequent reentry into the C state 204 would only require 3 seconds of time before the alarm were generated.

The reason that an alarm is not generated even through the C state 204 is entered is because sometimes infrastructure 105 becomes unstable but then parts of the infrastructure 105 move around and a new stable condition is obtained and no warning alarm is needed. However, if the unstable condition exists for a certain length of time TM then the unstable condition is unrecoverable and collapse will result. The alarm is different than the alert in that the user is told that a more severe condition is present. The alert can continue all the way until the alarm sounds, or once the B state 202 is exited the alert can be removed and nothing told to the user until the alarm is activated. However, in most arrangements, the alert will be given when the C state 204 is present before the alarm is given. The alerts and alarms can both be AE hit ratio numbers, or sounds of different intensity or different visual identifies such as lights or colors. The alarm may be distinctly different from the alert such that magnitudes or numbers are not associated with either but the user is simply instructed that one or the other is taking place.

Other arrangements of the system 47 are possible in which a time measurement of the system in the C state 204 of TM is not used to determine whether an alarm should be issued. In this other alarm initiation event, a threshold value is set and the system 47 looks at the data to determine whether the threshold value has been reached. The threshold value is determined based upon the factors of the amount of time that has elapsed in the C state 204 and the amount of hits that have occurred in this elapsed time in the C state 204. Looking at FIG. 9 as an example, the C state 204 is present from 1500-2000 seconds for a total of 500 seconds. The number of cumulative hits at the start of the C state 204 is 2500 and at the end of the C state 204 is 5500 for a total of 3000 hits during the C state 204.

The analysis may determine the area under the line of C state 204 and if this area equals a value A then the alarm is activated. If the area is less than the value A the alarm is not activated. In this manner, the generation of the alarm is based upon both time and hit quantity in the C state 204. The area under the line in the C state 204 could further be calculated in one of two different ways. The area may be calculated as the area 206 of the triangle below the line in the C state 204 with its base being the horizontal line 210 that is parallel to the x-axis and that starts at the initiation of the C state 204 at time 1500 seconds. Assuming that the value A is 1,000,000 the system 47 begins calculating the area A once the C state 204 begins. At time 2000 the area 206 is 0.5×500×3000=750,000 which is less than 1,000,000. The C state 204 ends at time 2000 seconds when the B state 202 is then identified. As the area 206 did not reach value A when in the C state 204 the alarm is not generated. However, if value A were instead 187,500 then this value A would be reached at time 1750 seconds when the calculated area A 206 is 0.5×250×1500=187,500. Once this value A is reached, the alarm is generated.

The second way of calculating the area under the line in the second alarm initiation event in the C state 204 is the calculation of an area that is equal to the area 206 plus the area 208. The calculation of the area 206 is as stated. Area 208 is calculated by taking the height of the line 210 on the y-axis times the amount of time on the x-axis. With reference to FIG. 9 area 208 is 2500×500=1,250,000. The area 206 is 750,000 at time 2000 seconds. Therefore, the total area under the line in the C state 204 all the way to the x-axis is area 206+area 208=750,000+1,250,000=2,000,000. If value A is 3,000,000 and the system goes back to the B state 202 at time 2000 seconds, then the value A has not been reached and the alarm is not generated. If the value A were some lesser number, then the sum of area 206+208 could be reached at some time between 1500 and 2000 seconds and the alarm generated in this alternative arrangement.

The alarm is generated in this second arrangement when the area under the line reaches a value A. The area under the line in the C state 204 could be calculated as the area 206, or could be calculated as the area 206+208 in accordance with different exemplary embodiments. If the value A is not reached before the C state 204 exits then the alarm is not generated.

The rational for this second alarm initiation event which uses area to determine whether to activate the alarm is based on the amplitude of the AE hits and the time duration during which this elevated AE hit rate is sustained. The higher the amplitude of the AE hits the less of time duration in the C state 204 is needed to determine that the infrastructure 105 is in a critical level of instability and structural failure is eminent.

The system 47 can be arranged so that the alarm is generated when the first alarm initiation event is detected, or when the second alarm initiation event is detected. The second alarm initiation event may be configured in either of the two ways previously described. Alternative exemplary embodiments also exist in which the system 47 monitors for both the first and second alarm initiation events when the system 47 detects the C state 204 and activates the alarm when the first one of the first or second alarm initiation events occurs. In this manner, both of the alarm initiation events are looked at and once one of them reaches their alarm state the alarm is sounded even though the other has not yet reached its alarm condition. In yet other arrangements, all of the alarm initiation events must be identified as occurring before an alarm is given. The alert described with respect to the system 47 identifying the B state 202 as being present may be included with this arrangement or may not be included with the embodiment in which the C state 204 is activated on one or both of the alarm initiation events.

The lines disclosed in FIGS. 8 and 9 are shown as being perfectly straight with transitions from one state to the next that have sharp corners and are abrupt. In other arrangements, the lines may not be perfectly straight but can be jagged or curved or of various shapes. Mechanisms for determining area under a curved or otherwise shaped lines are known. Further, the transition from one state to the next, for example from A state 200 to B state 202 may not be slightly curved or otherwise shaped such that it is not a sharp corner. The numbers disclosed are only for sake of example and others are possible in accordance with other exemplary embodiments.

The newly disclosed subject matter may incorporate all of the previously described components and arrangements. For example, the system 47 can be a newly installed system with the mine or other infrastructure 105 or may be a retrofit system that is installed at a later time. The time delay in learning the background noise may be the A state 200 or the A state 200 could be a state after the background/learning phase of the system 47.

While a present preferred embodiment of the invention is described, it is to be distinctly understood that the invention is not limited thereto, but may be otherwise embodied and practiced with the scope of the following claims.

What is claimed is:

1. A detection system for identifying deterioration in a structure, comprising:
   a sensor affixed to said structure and detecting a plurality of acoustic emission waves, each corresponding to a deterioration event;
   an analysis circuit having a processor receiving signals from said sensor representative of said deterioration events and identifying a corresponding first event rate, and a memory having first and second preselected factors stored therein at least partially defining first, second and third states, said analysis circuit establishing a base rate associated with said first event rate;
   said first state defined by an event rate less than said first event rate multiplied by said first preselected factor;
   said second state defined by an event rate greater than said first event rate multiplied by said first preselected factor and less than said first event rate multiplied by said second preselected factor;
   said third state defined by an event rate greater than at least said first event rate multiplied by said second preselected factor;
   said processor comparing a second event rate to said first event rate and correlating said second event rate to at least one of said first, second and third states; and
   said processor generating an alarm condition signal upon detection of said second event rate corresponding with said third state occurring for a preselected threshold time.

2. The detection system as set forth in claim 1, wherein said base rate is obtained during an initial time period defined between installation of said sensor and obtaining said second event rate.

3. The detection system as set forth in claim 1, further comprising an alarm in electronic communication with said analysis circuit, said alarm receiving said alarm condition signal from said processor and activating upon receiving said alarm condition signal.

4. The detection system as set forth in claim 3, wherein said alarm includes at least one of a visible indicator and a sound.

5. The detection system as set forth in claim 1, wherein said processor generates an alert condition signal upon detection of said second event rate corresponding with said second state, said processor stops generating said alert condition signal upon detection of said second rate event subsequently corresponding with said first state.

6. The detection system as set forth in claim 1, wherein said analysis circuit further comprises a counter measuring an amount of time said second event rate corresponds with said third state, said counter resetting upon said second event rate ceasing to correspond with said third state.

7. The detection system as set forth in claim 1, further comprising a plurality of sensors affixed to said structure, each of said plurality of sensors affixed to a different location in said structure.

8. The detection system as set forth in claim 1, wherein said acoustic emission waves originate in at least one of said structure and a matrix immediately adjacent said structure.

9. The detection system as set forth in claim 1, wherein said first event rate is in the range of greater than 0 event per second to 5 events per second.

10. The detection system as set forth in claim 1, wherein said first preselected factor is in the range of 0.5 to 5, and said second preselected factor is in the range of 2 to 15.

11. The detection system as set forth in claim 10, wherein said first preselected factor is 3 and said second preselected factor is 6.

12. The detection system as set forth in claim 10, wherein said first preselected factor is 4 and said second preselected factor is 9.

13. The detection system as set forth in claim 1, wherein said preselected threshold time is in the range of up to 1000 seconds.

14. The detection system as set forth in claim 13, wherein said preselected threshold time is five seconds.

15. A detection system for identifying deterioration in a structure, comprising:
a sensor that affixed to said structure and detecting a plurality of acoustic emission waves, each corresponding to a deterioration event;
an analysis circuit having a processor receiving signals from said sensor representative of said deterioration events and identifying a corresponding first event rate, and a memory having first and second preselected factors stored therein at least partially defining first, second and third states, said analysis circuit establishing a base rate associated with said first event rate;
said first state defined by an event rate less than said first event rate multiplied by said first preselected factor;
said second state defined by an event rate greater than said first event rate multiplied by said first preselected factor, and less than said first event rate multiplied by said second preselected factor;
said third state defined by an event rate greater than at least said first event rate multiplied by said second preselected factor;
said processor comparing a second event rate to said first event rate and correlating said second event rate to at least one of said first, second and third states; and
said processor calculating a realized area corresponding to a third state time and a third state event rate, wherein said third state time is the length of time said second event rate corresponds with said third state, and said third state event rate is the number of deterioration events detected during said third state time; and
said processor comparing said realized area to a predetermined alarm threshold value and generating an alarm condition signal upon detection of said second event rate corresponding with said third state and said realized area is at least equal to said predetermined alarm threshold value.

16. The detection system as set forth in claim 15, wherein said realized area is equal to 0.5 multiplied by said third state time multiplied by said third state event rate.

17. The detection system as set forth in claim 15, wherein said processor generates an alarm condition signal upon the earlier of:

1—detection of said second event rate corresponding with said third state and said realized area is at least equal to said predetermined alarm threshold; and
2—detection of said second event rate corresponding with said third state occurring for a preselected threshold time.

18. The detection system as set forth in claim 17, wherein said preselected threshold time in the range of up to 1000 seconds.

19. The detection system as set forth in claim 15, wherein said processor generates an alert condition signal upon detection of said second event rate corresponding with said second state, said processor stops generating said alert condition signal upon detection of said second rate event subsequently corresponding with said first state.

20. The detection system as set forth in claim 15, wherein said processor plots a graph of said signals from said sensor representative of said deterioration events over time, wherein said realized area corresponds to an area under the curve of said graph upon detection of said second event rate corresponding to said third state.

21. A method for identifying deterioration in a structure and an adjacent matrix, comprising the steps of:
affixing at least one sensor to said structure in receiving relation to acoustic emission waves emitted from said structure and said immediately adjacent matrix;
detecting said acoustic emission waves at said at least one sensor, each of said acoustic emission waves corresponding to a deterioration event;
establishing a first event rate corresponding to a base rate;
analyzing a second event rate of said acoustic emission waves detected over time and comparing said second event rate to a first and second preselected factors;
identifying a first state defined by an event rate less than said first event rate multiplied by said first preselected factor;
identifying a second state defined by an event rate greater than said first event rate multiplied by said first preselected factor, and less than said first event rate multiplied by said second preselected factor;
identifying a third state defined by an event rate greater than at least said first event rate multiplied by said second preselected factor;
comparing said second event rate to said first event rate and correlating said second event rate to at least one of said first, second and third states;
emitting an alert condition signal upon detection of said second event rate corresponding with said second state; and
emitting an alarm condition signal upon the earlier of:
1—detection of said second event rate corresponding with said third state occurring for a preselected threshold time; and
2—detection of said second event rate corresponding with said third state and a realized area is at least equal to a predetermined alarm threshold value; wherein said realized area corresponds to a third state time and a third state event rate, wherein said third state time is the length of time said second event rate corresponds with said third state, and said third state event rate is the number of deterioration events detected during said third state time.

* * * * *